United States Patent [19]
Silman

[11] Patent Number: 4,753,878
[45] Date of Patent: * Jun. 28, 1988

[54] MICROORGANISM IDENTIFICATION TECHNIQUE

[75] Inventor: Robert E. Silman, London, England

[73] Assignee: AMB Systems Corp., San Diego, Calif.

[*] Notice: The portion of the term of this patent subsequent to Jun. 4, 2002 has been disclaimed.

[21] Appl. No.: 729,792

[22] Filed: May 2, 1985

Related U.S. Application Data

[60] Division of Ser. No. 426,196, Sep. 28, 1982, Pat. No. 4,521,512, which is a continuation-in-part of Ser. No. 341,810, Jan. 22, 1982, Pat. No. 4,526,865.

[51] Int. Cl.⁴ .............................................. C12Q 1/16
[52] U.S. Cl. ..................................................... 435/35
[58] Field of Search ....................... 435/29, 34, 35, 38, 435/814, 808, 803, 820; 436/56, 63; 204/403

[56] References Cited

U.S. PATENT DOCUMENTS 4,521,512  6/1985  Silman .................................. 435/34
4,526,865  7/1985  Silman .................................. 435/38

OTHER PUBLICATIONS

Metzler, "Biochemistry" Academic Press (1977) NY, pp. 124–125.
Winkelman et al "Automatic Calculation of Densitometer Scans of Electrical Strips" Clinical Chemistry 15(8) pp. 708–711 (1969).

Primary Examiner—John E. Tarcza
Attorney, Agent, or Firm—Michael Ebert

[57] ABSTRACT

A technique for identifying an unknown microorganism, in which technique a specimen of the unknown microorganism is prepared to which a radioactive emissive agent has been added that is actively incorporated into the products of metabolism of the microorganism to produce a mix of radioactive peptide or protein emissive products in a manner that depends on the metabolic mechanism of the microorganism. The peptide or protein emissive products in the mix resulting from the preparation of the specimen are then separated. The separated emissive products are detected by sensing the emission from the products to provide an electrical signal whose wave pattern is indicative of the identity of the microorganism. This wave pattern is compared in a computer with patterns stored therein representing a collection of known microorganisms.

3 Claims, 2 Drawing Sheets

MICROORGANISM IDENTIFICATION TECHNIQUE

RELATED APPLICATIONS

This application is a division of the copending application Ser. No. 426,196 of the same title, filed Sept. 28, 1982, now U.S. Pat. No. 4,521,512 which in turn is a continuation-in-part of application Ser. No. 341,810, filed Jan. 22, 1982, now U.S. Pat. No. 4,526,865.

FIELD OF THE INVENTION

The invention relates to a method for the identification of microorganisms and especially to such a method wherein an identifier is generated for the microorganisms which is then compared with a collection of identifiers representing various known microorganisms to find whether there is a match with one thereof, the comparison preferably being automated.

BACKGROUND TO THE INVENTION

In microbiology, microorganisms are classified in taxonomic categories, nomenclature being used to name the units delineated and characterised by classification. Identification by classical procedures involves the use of criteria established for classification and nomenclature in order to identify microorganisms by comparing the characteristics of an unknown unit with known units. Thus with a newly isolated microorganism, its identification requires an adequate characterisation thereof and then a comparison with published descriptions of other similar micoogranisms.

To identify an organism of interest that is present in a specimen of mineral, plant or animal origin, it is first necessary to obtain an isolated colony of the microorganism. There are well developed procedures for growing or cultivating microorganisms in the laboratory on nutrient material, some of these procedures requiring special conditions such as the absence of free oxygen. By incubating a nutrient agar-type medium, using the streak-plate or pour-plate method, cells are individually separated. In incubation, individual cells reproduce rapidly to generate a visible colony of cells, each colony being a pure sample of a single kind of microorganism.

In order to identify an unknown cell, classical techniques call for the use of high-magnification optical or electron microscopes in order to determine colony and cell morphology. In addition numerous other characteristics may have to be determined, including staining characteristics, susceptibility to antimetabolites and serological and biochemical properties. The procedures for the identification of bacteria are set forth in detail in chapter 5 of the text "Clinical Bacteriology"-Fifth Ed.—J. Stokes et al., published by Arnold (London) 1980.

Thus, the identification of microorganisms by classical techniques is time-consuming, labour-intensive and expensive and, not withstanding the high order of technical skill required, is liable to error.

The identification of microorganisms is clearly of great importance in the medical and veterinary fields. However, in recent years the need for efficient and relatively rapid identification techniques has become even more pressing owing to the remarkable expansion of environmental and industrial microbiology. Thus, the cultivation of microorganisms in food processing, in the fermentation of alcoholic beverages, and in the manufacture of pharmaceuticals and of such industrial reagents as the alcohols and acetic acid is already well established. The use of microorganisms has been proposed not only for syntheses but also for counter-pollution measures; an interesting use of selected microorganisms to degrade products of industrial organic syntheses is described in GB-A-2010327. Furthermore, genetic engineering is expected markedly to increase the range of applications of microbiology in industry and agriculture (see Scientific American, September 1981).

There have, of course, been attempts to improve upon the classical techniques for microorganism identification. For example, Tsukamura and Mizuno (Kekkaku 1980, 55 (12) pages 525-530) disclose a method by which certain selected microorganisms can be distinguished. The precultured organism was incubated for 24 hours in a reaction medium containing L-$^{35}$S-methionine, after which the cells were centrifuged, washed and extracted with ethyl ether/ethanol. The extracted material was subjected to further extraction using petroleum ether and the resultant material was subjected to thin-layer chromatography. Any radioactive spots in the thin-layer were detected by an automatic scanner. These Japanese workers were able to distinguish Mycobacterium nonchromogenicum (which gave one strong radioactive spot at an Rf value 0.70-0.80) from M.terrae and M.triviale (which two organisms produced no spot or only a trace spot). They were also able to differentiate between two particular Rhodococcus species and to distinguish Rhodococcus species from Nocardia species (the former giving a spot at Rf 0.10 or Rf 0.95, whereas Nocardia displayed no such spots).

The method described in the Kekkaku article clearly does not qualify as a general method for the identification of microorganisms: thus, the Japanese workers were unable to differentiate M.terrae and M.triviale. Furthermore, the method required an initially high concentration of microorganism and a long incubation period in the $^{35}$S-methionine-containing medium. An interesting observation is that, although methionine is an amino acid (such acids being the building blocks of proteins), the petroleum ether extraction would not have taken up proteins and thin-layer chromatography (11 C) is not a useful technique for resolving proteins. It would appear, therefore, that any radioactive spot that may be detected in the thin layer is not due to the incorporation of the $^{35}$S-methionine in a protein product of the metabolism of the organism, but is due to a product of a secondary reaction between the radioactive label and a compound derived from the organism.

With a view to automating the identification of microorganisms U.S. Pat. No. 4,288,543 to Sielaff et al. discloses a procedure in which the susceptibility of various strains of bacteria to antimicrobial agents is tested, this being done in conjunction with a determination of the light-scattering index of the organism being tested. The numerical growth data obtained by the light scatter comparisons are analysed by computer-assisted statistical techniques in order to identify the organism. The admitted drawback to this procedure is that one should use agents not in common therapeutic use in order to avoid errors resulting from strains that have become immune to various therapeutically utilised antibiotic agents. Furthermore, it is necessary to divide the initial sample of the microorganism (specifically a bacterium) into a number of sub-samples, each of which has to be inoculated with a respective growth-inhibiting agent, incubated and then tested. The Sielaff patent also makes of record other publications dealing with the automated identification of bacteria by computer analysis of growth inhibition patterns.

The logical approach to the problem of identification is to find or create an identifier, namely a characteristic by means of which the identity of an unknown can be determined. Thus, fingerprints are regarded as identifiers for human beings, since a person can be identified by his fingerprints alone, without reference to that person's other characteristics, such as sex, age, height, weight, shape, eye colour and the like. However, a problem in applying this approach to microbiology is the difficulty of selecting a microorganism characteristic that really is an identifier, that can be routinely utilised as such, and that is applicable throughout the group of microorganism (especially bacteria) in question. The identifier, like a fingerprint, should be substantially universal. Obviously, like human fingerprints, there may be exceptions, but the generation of the identifier should be the rule and not the exception.

One attempt to tackle this problem is described in GB-A-1489255. That specification describes a process for the identification of a microorganism which comprises inoculating a plurality of different $^{14}C$-labelled substrates with an unknown organism and incubating the substrates for a time sufficient to cause metabolic breakdown of at least some of the substrates by the organism to produce the radioactive gas $^{14}CO_2$. The gas that is evolved is analysed for radioactivity in order to obtain a "substrate radiorespirometric profile" for the unknown microorganism. Such a profile is said (page 3, lines 3–13) to serve as a fingerprint of the unknown microorganism, in that the profile can be compared to standard profiles obtained in the same manner from known microbes. That technique requires the unknown microorganism to be tested against a sufficient number of substrates taken individually in order to obtain a meaningful profile; for instance, in the specific Example of GB-A-1489255, thirty substrates are used. Thus, each unknown is subjected, in effect, to a series of complex tests and this must render it difficult to standardise the test procedure.

SUMMARY OF THE INVENTION

The present invention now provides a method for identifying microorganisms comprising the steps of: adding to a specimen of microorganisms an emissive agent that is incorporated therein to produce a mix of emissive products in a manner that depends on the metabolic mechanism of the microorganisms; detecting the emissive products to derive a characteristic pattern functioning as an identifier of the microorganisms; and comparing the said identifier of the microorganisms with a collection of identifiers representing known microorganisms (the collection conveniently being in the form of stored information) to determine the identity of the microorganisms.

Herein, the expression "metabolic mechanism" is to be broadly construed and includes catabolic and genetic mechanism.

Identification, for the purposes of this specification, encompasses the determination of whether the microorganisms in the specimen (which may be referred to as the "unknown" microorganisms) fall within a particular group. Identification can be carried out at various levels: thus, it may be sufficient to identify the microorganisms as being of a particular Family or Genus, although commonly one would wish to determine the Species or even the Subspecies, Strain or Serotype of the microorganisms in question.

The present method can also be used to quantify the microorganisms since the overall intensity of the emission from the mix will be proportional to the quantity of the microorganism that produces the mix.

The microorganisms in the specimen may, for example, be bacteria or fungi (which term includes the yeasts).

However the method is also applicable to the identification of those microorganisms, in particular viruses or other obligate parasites such as Rickettsia and Chlamydia, that require a host cell for metabolic activity. Accordingly, the expression "mix of emissive products" is to be construed in such cases as referring to the mix produced by the microorganism and its host cell together. Here the identifier for the microorganism may be generated by altering the metabolism of the host cell as much as by the generation of its own products.

DESCRIPTION OF THE PREFERRED EMBODIMENTS

Figure 1:
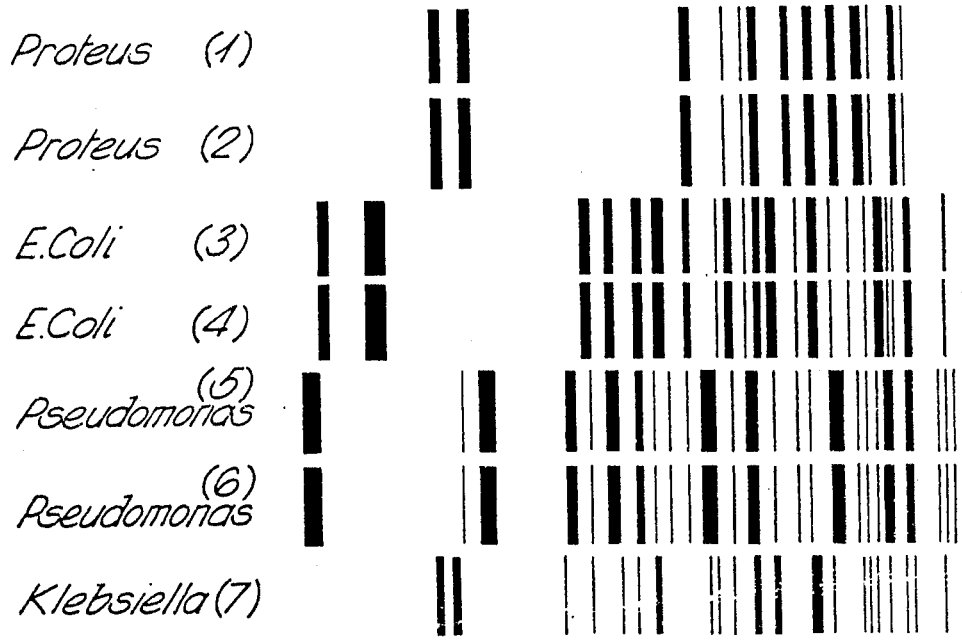
FIG. 1 gives examples of band patterns derived from different types of bacteria by a method in accordance with the invention.

The present invention is based on a discovery unexpectedly made in the course of research in which the function of messenger RNA (ribonucleic acid) in particular tissues was being investigated. In this investigation, messenger RNA was extracted from tissue and purified. Then the messenger RNA was translated into corresponding protein by adding thereto a cell-free system constituted by a ribosomal mixture with little or no genetic information of its own, but having the capacity to translate exogenous messenger RNA. As a consequence, the free amino acids in the translation medium were incorporated into the protein in a sequence dictated by the messenger RNA derived from the tissue.

In order to identify the products of the translation system, a radioactive sulphur-containing amino acid ($^{35}S$-methionine) was added to the system.

After a translation period lasting about two hours, the translation medium was layered onto a gel plate and subjected to electrophoresis. Electrophoresis is the migration of colloidal particles in a liquid due to a potential difference established across immersed electrodes, the migration being toward the electrode having a charge opposed to that of the particles. Electrophoresis is applicable to a protein, for its molecules act as colloidal particles, and their charge is negative or positive, depending on whether the surrounding solution is acidic or basic.

All free amino acids ran through the system, while all amino acids which had been incorporated into newly translated proteins were adsorbed on the plate at chromatographic positions characteristic of the protein into which they had been incorporated. Similarly, any $^{35}S$-methionine which had been incorporated into a protein would be retained within it and thereby function as a marker for the molecules.

The gel plate was then placed against a sensitive photographic plate. Appearing on the photographic plate as a result of radioactive emission (beta radiation) from the $^{35}$S-methionine, were bands occupying positions thereon appropriate to the molecule in which the radioactive amino acid had been incorporated.

In this plate, the bands had an intensity proportional to the amount of $^{35}$S-methionine incorporated into the protein, i.e. to the number of methionine amino acids in the protein and to the quantity of the protein that had been synthesized.

One would expect, when following this procedure, that in the absence of a message, no bands except for endogenous background translation would appear on the photographic plate. But contrary to this expectation, bands were developed which did not seem to correspond in any way to the messenger RNA that had been added to the translation system. Moreover, it was found that bands were created even when no RNA from any source whatever had been added to the system.

The conclusion then reached was that the unexpected appearance of bands could only be imputed to bacterial contamination, and that it was bacterial RNA that was being translated. This conclusion was confirmed when the bands were caused to disappear by sterilizing the various solutions that were being used in this research programme.

It was also observed that different solutions gave rise to different band patterns, each solution producing a unique pattern quite distinct from those emanating from the other solutions. It was discovered that these distinctive band patterns occurred because the solution from which they were derived were contaminated with different types of bacteria, each generating a different pattern of translated proteins. This led to a principle underlying the present invention, namely that microorganisms, for example bacteria, can be identified by their pattern of emissive products, for example radioactive proteins.

In principle, any emissive agent can be used in the practice of this invention, provided that the agent is incorporated into products of metabolism that will serve as identifier for the microorganism in question. Thus, use could be made of emissive nucleic acids, long-chain fatty acids, carbohydrates and membrane units to produce a mix of emissive products. As long as this mix is the result of the specific metabolism of the microorganism and can thereby be used to identify the microorganism, it does not matter where or how the metabolic mechanism is being harnessed. However, the use of an emissive amino acid is preferred, since in general it will be incorporated in a range of protein products which will serve as a particularly useful identifier for the microorganism under investigation.

The use of an emission, such as radioactivity, fluorescence or the like, is necessary to be able to detect the newly translated products, such as proteins, that are present in minute quantities, in general of the order of picograms or femtograms. Thus, it is preferred that the emissive agent should contain a radioactive element such as $^{35}$S, $^{32}$P, $^{14}$C, $^3$H or $^{125}$I. The use of a radioactive amino acid as the emissive agent is especially preferred, examples being $^3$H-leucine, $^{14}$C-lysine and, especially, $^{35}$S-methionine.

The emissive agent may be added to the specimen by placing the microorganisms in a medium, to which the emissive agent is added (before, during or after the placcement of the organisms), incubating the resultant medium for a period and arresting the incubation reaction at the end of that period.

For example, a culture medium containing the microorganisms to be identified, if appropriate after dilution, may have added thereto the emissive agent, if appropriate as a solution thereof. Alternatively, the culture step can be bypassed and the sample containing the microorganism can be obtained from source and the emissive agent added directly. After a predetermined incubation period (for example two hours), the reaction is arrested, for example by the addition of one or more appropriate chemical agents, such as sodium dodooyl sulfate (SDS) and mercaptoethanol. In the preferred embodiments, SDS also serves a useful function, in that it acts to break down aggregates of proteins that may have formed, as by hydrogen bonding.

In general, it will be necessary to subject the resultant mix of emissive products to separation in order to "display" the unique characteristics thereof. An acceptable method for protein separation is isoelectric focusing, in which proteins are caused to separate, across a substrate for example in the form of a plate, and to fix themselves at their isoelectric points. Affinity, molecular-sieve and ion-exchange chromatography may also be used for separation, as may isotachophoresis.

In preferred embodiments, separation is effected by electrophoresis, since this is a highly discriminating method for segregating proteins. Thus, after the incubation reaction has been arrested, the inoculated culture medium may be layered on to a suitable substrate, for example a polyacrylamide gel, conveniently in the form of a plate, where it is then subjected to electrophoresis.

While each emissive product in a mix obtained from a given organism may be found in mixes derived from other organisms, it appears that the mix obtained from a given organism is uniquely characterised by the nature of the products present and by their relative proportions. To that extent, the identifier for the microorganism under investigation is already implicit in the mix of emissive products. However, it is necessary to detect the emissive products in order to obtain a characteristic pattern that will permit the comparison step necessary to effect identification. As indicated above, the detection is generally proceded by a separation step in order, as it were, to "reveal" the components of the mix. It may in some cases be sufficient for identification purposes simply to determine the relative positions of the components in the resultant array or "spectrum" of separated or segregated emissive products. In other cases it may also be necessary to determine the relative proportions of the products, as by detecting the relative intensity of the emissions from the individual products.

The emissive products may be detected by exposing an appropriately sensitive film to the emission from the said products. Thus, in embodiments wherein radioactively emissive products have been subjected to electrophoresis on a gel substrate, the latter may be autoradiographed by placing it adjacent to an X-ray film for a period sufficient to produce in that film a characteristic band pattern; the latter will in general resemble a bar code pattern and may be referred to as such.

As indicated above, an unknown microorganism can be identified by finding a match of the identifier for that unknown with one of a collection of identifiers representing various known microorganisms. Thus, the band pattern in the film, once fixed, may be compared to the band patterns obtained in an analogous manner from known microorganisms.

The autoradiographs obtained as described above, although permitting visual comparisons to be effected, are also machine-readable, in that the band pattern may be sensed electrooptically by means adapted to provide a corresponding electrical signal pattern.

It is also possible to dispense with the autoradiographing step and to detect directly the emissive products by sensing the emission therefrom by means adapted to provide a corresponding electrical signal pattern which can be processed to give a print-out in a desired graphical form for visual comparison with print-outs obtained analogously from known microorganisms.

However, the electrical signal pattern obtained by direct sensing of the emissive products or by sensing of an autoradiograph may be processed in a computer to perform identification procedures; thus, the obtained electrical signal pattern may be compared in a computer with patterns stored in the computer memory, said stored patterns representing a collection of known microorganisms. The stored patterns constitute a library of identifiers which can be created by subjecting each of a number of known microorganisms to the emissive-agent addition, incubation, separation and detecting steps described above. The comparison may be effected by automated pattern recognition techniques known in principle. Pattern recognition entails the steps of feature extraction and then of classification using statistical analysis. Such techniques are described in "Pattern Recognition, a Statistical Approach" by P. A. Devijver and J. Kittler published by Prentice Hall, London (1982).

Figure 3:
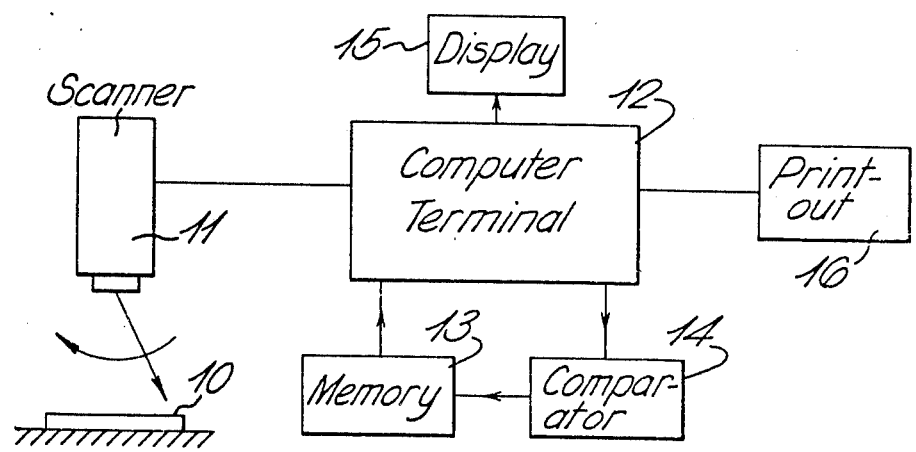
FIG. 3 is a simplified block diagram of a computerised system for automatically carrying out an identification procedure in accordance with the invention.

Referring now to FIG. 3, there is shown a computerised system for scanning a band pattern formed on a radiographic plate 10, the pattern being an identifier for an unknown microorganism.

This pattern is electro-optically scanned by a scanner 11. In principle, it is immaterial whether the scanner moves along a stationary plate, or the plate is moved beneath a stationary scanner. The scanner comprises a light-sensitive element, for example a photo-electric cell, and may be responsive not only to the absence or presence of bands but also to variations in the intensity of those bands.

The output of scanner 11 is converted into digitised signals for processing in a computer terminal 12. Computer terminal 12 operates in conjuction with a memory 13 in which is stored a library of band patterns of known forms of microorganism.

The function of the computer system is to identify the unknown microorganism whose band pattern has been scanned. To this end an electronic comparator or the equivalent software 14 is provided to find a match between the input signals and one of the stored patterns representing various known forms of microorganisms. When a match is found, information is conveyed to computer terminal 12 whose output then provides on a visual display 15 a read-out of the identified microorganisms, and on an associated print-out 16, a hard copy of the reading.

Direct scanning of the separated emissive products can be effected by means of apparatus analogous to that shown in FIG. 3, except that the plate 10 would be replaced by a substrate bearing the separated emissive products and that, where the emission is radioactivity, the electro-optical scanner 11 is replaced by a suitable radiation counter such as a Geiger counter.

Alternatively, a video camera may be used, whereby the emissions are caused to impinge on a plate sensitive thereto, the plate being scanned by an electron beam to generate a video signal. The video signal may then be digitised and processed in a computer to effect identification.

In practice, the computer may store not only the names of known microorganisms, but also data in regard to the nature and characteristics thereof. These stored data can be printed out, so that the user of the system is informed not only as to the identity of the unknown microorganism, but also useful information relevant thereto.

Another approach obviating the need for visual inspection of the band pattern in determining the identity of an unknown microorganism is to electro-optically scan the pattern to produce a signal which is converted into a multi-digit code number unique to the pattern. A scanning system capable of converting a pattern into a unique code number is disclosed in the U.S. Pat. No. 3,581,282 to Altman wherein the pattern is that produced by the palm of the hand, the Altman system serving to identify individuals.

By converting band patterns into code numbers in the manner taught by Altman, one can then create a directory of code numbers and in which each code number is related to a known type or strain of microorganisms. Thus one who wishes to identify an unknown microorganism first produces a radiograph in the manner disclosed hereinabove, and then by means of a scanning system of the Altman type, converts the band pattern into a code number. Once he has the code number, it becomes a simple matter to consult the code directory to fix the identity of the unknown microorganism.

As pointed out previously, for purposes of identification it may not always be necessary to find the exact identity of the microbe, and to determine for example that the microbe is *E. coli*, serotype 06. In some situations, it may be sufficient for purposes of identification to determine whether the unknown is of a particular genus. To this end the computer may be governed by an algorithm or programme operating in conjunction with an appropriate data bank so as to process the output of the scanner or detector to identify the unknown with respect only to genus or whatever other taxonomical description is required.

Thus, the process of identification in the context of the present invention, lies in determining whether an unknown microbe lies within or matches a genus, a species, a strain or any other established or predetermined frame of reference. In that sense, a system in accordance with the invention may have a degree of resolution that depends on the task assigned thereto.

It is desirable in order to provide a constant identifier unique to each microorganism, that the conditions under which the pattern is produced be standardised. To facilitate standardisation a reference standard may be established in a form which can be fed as reference data into a computer. Subsequent samples may thereafter be checked by the computer with the reference to see whether a search lies within an acceptable tolerance band. Under standardised conditions, the pattern from a given microorganism is always substantially the same.

To overcome difficulties in maintaining absolutely standard conditions for determinations, the detection system may be calibrated, for example by detecting the emission products of a known control, which emission products have been obtained and separated under the same conditions as the emission products of the unknown. The signal of the unknown is then modified (to a degree determined by the difference between the control signal and a corresponding signal stored in the data bank) in order to obtain a proper comparison of the unknown with the stored data.

Commonly, the microorganisms in the specimen to which the emissive agent is added will be of a single kind, i.e. the microorganisms will be substantially identical, as in a pure culture. However, the present method can in appropriate circumstances be applied to specimens comprising a mixture of microorganisms. Thus, it would be possible to create a library of "composite identifiers" each representing a mixture of microorganisms that commonly occur together. Furthermore, it may be possible to identify the members of a mixture of microorganisms from a composite identifier obtained therefrom by using computer "subtraction" techniques already known in principle.

The present invention shares the advantages of known automated identification techniques, for example it can dispense with the need for interpretation of results by experienced technicians, since the identification can be effected automatically. In addition, the present method exhibits a number of other advantages, not least in the simplicity and comparative speed with which the identifier can be obtained. Thus, in contrast to the techniques in U.S. Pat. No. 4,288,543 and GB-A-1,489,255 mentioned above, the specimen of microorganisms need be reacted with only one substrate.

The present invention permits the production of the identifier in the form of stored information (e.g. as an autoradiograph, as a printed graphical representation or as data in a computer memory) that admits of ready comparison with similarly obtained identifiers of known organisms.

Also, in contrast to Tsukamura et al. above, not only is the present method quick (compare the twenty-four-hour incubation period and extraction procedures employed by Tsukamura et al., despite the initial high concentration of the microbe), but also the present method has been used to identify all bacteria so far studied. Thus, Tsukamura et al. were confined to the further characterisation of a few specific organisms that had already been classified, since they investigated only the absence or presence of specific products, as detected by TLC. That approach depends on the finding of specific products to identify a microorganism. By contrast, in the present method it is the pattern of non-specific products, none of which have been selected and none of which may be unique, which provides the identifier.

Another advantage of the present method is that it is possible to bypass the culture stage and directly to identify a microorganism taken from source (e.g. water, soil, urine, cerebrospinal fluid).

A further advantage of the present method is that it can be used not only to identify known organisms, but also to discover new ones, thus, if the identifier obtained from an unknown microorganism fails to match any identifier in the library of known microorganisms, it would be possible to assign a name to that unknown, whereupon its identifier may be added to the library in order to create a new "known" organism. For example, the organism C. difficile has proved difficult to classify and specimens have hitherto been referred to by isolate numbers. By means of the present method, it is possible to determine which of the isolates are, in fact, identical and then to classify the different strains. Thus, the present method can be used to classify microorganisms to create a taxonomy with reference to those subsequent identifications.

The present invention is illustrated by the following specific Examples.

EXAMPLE 1

To identify different types of bacteria, a 1/100 dilution was made of culture mediums containing Proteus, E. coli, Pseudomonas and Klebsiclla, each cultured in duplicate.

Five microlitres of solution was taken from each sample, to which was added five microlitres of L-$^{35}$S-methionine. No translation system was added. After a two-hour incubation period, the reaction was arrested by adding 10% SDS (sodium dodecyl sulfate) and 3% mercaptoethanol in trisbuffer. After heating, each solution was then layered onto a polyacrylamide gel plate. After carrying out electrophoresis for sixteen hours at 70 volts or 2.5 hours at 200 volts, the gel was fixed for three hours, dehydrated with acetic acid washes and exposed to a 2,5-diphenyloxazole/acetic acid mixture for three hours. The plate was then water-washed and dried to provide the desired specimen. Finally the plate was autoradiographed by exposing the gel to an X-ray film overnight.

A trace of the resultant autoradiograph is shown in FIG. 1 wherein channels 1 and 2 are the duplicates of Proteus; channels 3 and 4, the duplicates of E. coli; channels 5 and 6, the duplicates of Pseudomonas; and channel 7, Klebsiella.

It will be evident from an examination of FIG. 1 that the pattern of bands in channels 1 and 2 are identical so that duplicate samples of Proteus give rise to the same bar code identifier. This is also true of E. coli in channels 3 and 4 or Pseudomonas in channels 5 and 6; and Klebsiella in channel 7 is different from the other bar codes. The products are located by their position and the distribution around that position (as reflected by the resolution of the separation technique).

EXAMPLE 2

The procedure described in Example 1 was repeated for a second five microlitres from each of the cultures. The resultant autoradiograph was indistinguishable from that shown in FIG. 1, thereby indicating that under standardised conditions, each bacterium gave rise to a distinctive band pattern readily distinguishable from those produced by the other bacteria. It is therefore possible with the naked eye to identify each bacterium by means of its autoradiographed identifier.

EXAMPLE 3

(A) To determine whether it was possible to identify different serotypes within a single bacterial type, three different serotypes of E. coli were cultured in duplicate (01-06-075) and treated in the same manner as described in Example 1 to produce an autoradiograph.

Figure 2:
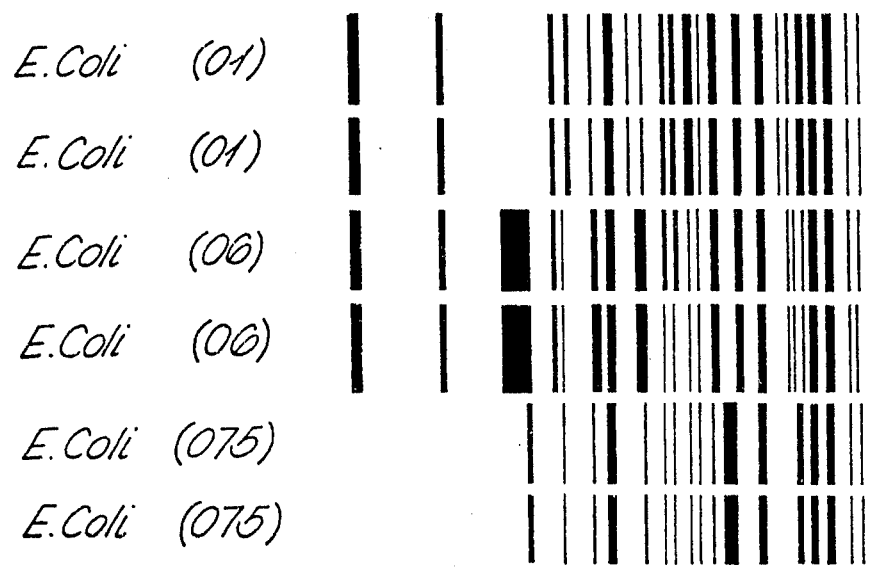
FIG. 2 gives examples of band patterns derived from different serotypes of a single type of bacteria.

As shown in FIG. 2, the band patterns for the duplicate 01 serotype are the same, this being true of the band patterns for the duplicate 06 and 075 serotypes. But there are significant differences in the band patterns for the different serotypes which serve to distinguish the identifiers from each other. Although the differences in this case are not as pronounced as when different genera of bacteria are involved, it is clear that the present identification method is capable of a fine degree of resolution.

(B) In another experiment six different serotypes of *E. coli* were cultured in duplicate. One set of duplicates was labelled with the name of the serotype (01, 06, 075, 040, 0108) and the other set was given a code number.

Fifty microliters of sample were taken from each culture incubated with approx. 5 μCi (5 μl) of $^{35}$S-methionine (1385 Ci/mmol) for two hours at 37° C. The incubation was stopped by the addition of 55 μl SDS/PAGE sample buffer (4% SDS, 6% mercaptoethanol, 4% glycerol in Tris/HCl, pH 6.7) and the sample was then heated. Twenty-five microlitres from the mixture was loaded onto a 1% SDS/12.5% polyacrylamide gel (16 cm × 18 cm). Twelve samples were loaded onto one gel plate. The plate was electrophoresed at 70 volts overnight in a cold room after which it was fixed (20% acetic acid, 20% isopropanol in water), fluorographed (EN$^3$ HANCE, New England Nuclear), dried and then exposed to X-ray film (Fuji RX) for three days at −70° C. The six serotypes of *E. coli* in the named samples gave six distinct band patterns upon autoradiography, these patterns being different from one another. It proved possible for three investigators, who were ignorant of the code, independently to discern the correct match between each of these band patterns and the band pattern of the corresponding code-numbered sample.

This experiment shows that it is quite possible to distinguish different serotypes of the same microorganism by means of the present invention. Ordinarily, the identification of serotypes is a time-consuming affair which requires the raising of antisera and the performing of agglutination tests against the O and the H antigens of the microorganism.

In the procedure described above in Example 3 (B), the array of radioactive proteins obtained after electrophoresis is fluorographed. Fluorography is employed in order to enhance the exposure of the film and entails the addition of a substance which will emit light upon stimulation with radioactivity. Thus, fluorography may be utilised as part of the detection step in the present process. Fluorography may be particularly advantageous when the emissive agent comprises tritium ($^3$H) as the radioactive element.

EXAMPLE 4

In a manner analogous to that described in Example 3(B), six different serotypes of *E. coli* were incubated in a medium containing $^{35}$S-methionine and then subjected to electrophoresis in order to obtain, for each serotype, an array of segregated emissive protein products.

The segregated products were detected by direct scanning by mounting the polyacrylamide gel strips containing the products on a conveyor and passing the strips beneath a collimated geiger counter functioning as the scanner in an apparatus substantially as described above with reference to FIG. 3. The scanner was interfaced with an ITT 2020 microcomputer which in turn was interfaced with a visual display unit (VDU), floppy disc drives and a printer.

The pattern for each serotype was displayed on the VDU and a hard copy was obtained from the printer, the pattern being presented in the manner of a histogram. The patterns from the serotypes were clearly distinguishable one from another.

EXAMPLE 5

The microorganisms mentioned in Examples 1 to 4 above are all gram negative aerobic bacteria. An analogous procedure to that described in Example 1 has been successfully employed for the identification of various gram positive aerobic bacteria, such as *Staphylococcus aureus* and *Streptococcus faecalis*, as well as gram positive anaerobic bacteria such as *Clostridium perfringens, C. bifermentans, C. butyricum* and *C. difficile* (including subgroups of the isolation numbers) and gram negative anaerobic bacteria such as *Bacteroides bivius, B. thetaiotamicron, B. vulgatus, B. corrodens, B. ovatus, B. distasonis* and *B. fragilis* (including various serotypes thereof); for the identification of a yeast (*Candida albicans*); for the identification of Gonococcus species; and for the identification of a mixture of organisms (*E. coli* and Proteus sp.).

EXAMPLE 6

Host cells (human embryonic lung fibroblast cells) were grown for a period of 24–48 hours in specimen tubes using a minimum essential medium (1 ml for each tube). 5–10 μl (5 μCi) of $^{35}$S-methionine were added to each tube, which was subsequently inoculated with a virus, either Herpes simplex 1 or Herpes simplex 2. The tubes were incubated for various periods of time ranging from 1 to 4 days. One tube was harvested daily as follows. The supernatent was first poured off and then trypsine was added. 50 μl of the resultant slurry was added to 50 μl SDS/PAGE buffer solution. The sample was then loaded onto a polyacrylamide gel plate and subjected to electrophoresis as described above.

The segregated, emissive protein products were detected by means of autoradiography. The band pattern obtained from the H. simplex 1/host cell entity was clearly distinguishable from that obtained from the H. simplex 2/host cell entity.

I claim:

1. A technique for identifying an unknown microorganism comprising the steps of:
    A. preparing a specimen of the microorganism to which a radioactive emissive agent has been added that is actively incorporated into the products of metabolism of the microorganism to produce a mix of radioactive peptide or protein emissive products in a manner that depends on the metabolic mechanism of the microorganism;
    B. separating the peptide or protein emissive products in the mix resulting from said preparation of a specimen;
    C. detecting the separated peptide or protein emissive products by sensing the emission from the products to provide an electrical signal whose wave pattern is indicative of the identify of the microorganism; and
    D. comparing the wave pattern derived from the unknown microorganism with a collection of wave patterns representing known organisms in order to determine the identity of the unknown organism.

2. A technique as set forth in claim 1, wherein said wave pattern derived from the unknown microorganism is compared in a computer with patterns stored in the computer memory representing a collection of known microorganisms.

3. A technique as set forth in claim 2, wherein the computer is a digital computer and the wave pattern of the unknown microorganism is in the form of a video signal that is then digitized and processed in the computer.

* * * * *